United States Patent
Hao et al.

(10) Patent No.: US 6,953,434 B2
(45) Date of Patent: Oct. 11, 2005

(54) METHOD AND APPARATUS TO ENHANCE ULTRASOUND CONTRAST IMAGING USING STEPPED-CHIRP WAVEFORMS

(75) Inventors: Xiaohui Hao, Waukesha, WI (US); Satchi Panda, Greenfield, WI (US); Steven C. Miller, Pewaukee, WI (US); Richard Y. Chiao, Menomonee Falls, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 355 days.

(21) Appl. No.: 10/065,180

(22) Filed: Sep. 24, 2002

(65) Prior Publication Data

US 2004/0059225 A1 Mar. 25, 2004

(51) Int. Cl.[7] .............................................. A61B 8/06
(52) U.S. Cl. ...................................................... 600/458
(58) Field of Search ................................ 600/437, 443, 600/447, 458

(56) References Cited

U.S. PATENT DOCUMENTS

| | | | |
|---|---|---|---|
| 5,966,169 A | 10/1999 | Bullis | |
| 6,117,082 A | * 9/2000 | Bradley et al. | 600/447 |
| 6,193,663 B1 | * 2/2001 | Napolitano et al. | 600/447 |
| 6,213,947 B1 | * 4/2001 | Phillips | 600/443 |
| 6,371,914 B1 | * 4/2002 | Arditi | 600/443 |
| 6,401,539 B1 | 6/2002 | Langdon et al. | |
| 6,440,074 B1 | * 8/2002 | Averkiou | 600/443 |

* cited by examiner

*Primary Examiner*—Francis J. Jaworski
(74) *Attorney, Agent, or Firm*—McAndrews, Held & Malloy, Ltd.; Peter J. Vogel; Michael A. Dellapenna (57) ABSTRACT

A method and apparatus in an ultrasound imaging system is disclosed that enhances the contrast-to-tissue ratio and signal-to-noise ratio of contrast imaging using stepped-chirp waveforms. The first waveform component is employed with a first frequency optimized to initiate the bubble dynamics and the second waveform component is employed with a second frequency optimized to produce an enhanced bubble nonlinear response. The first waveform component and the at least a second waveform component are transmitted as a single stepped-chirp transmit pulse. At least one of a center frequency, an amplitude, a starting phase, and a bandwidth of the waveform components are adjusted to generate the single stepped-chirp transmit pulse. A relative phase, a switch time, and a time delay between the waveform components are also adjusted for maximal enhancement of bubble nonlinear response.

32 Claims, 8 Drawing Sheets

0 degree    180 degree

☐ Compression half period

▨ Expansion half period

METHOD AND APPARATUS TO ENHANCE ULTRASOUND CONTRAST IMAGING USING STEPPED-CHIRP WAVEFORMS

BACKGROUND OF THE INVENTION

Certain embodiments of the present invention relate to contrast imaging in ultrasound. More particularly, certain embodiments relate to enhancing contrast-to-tissue ratio (CTR) and signal-to-noise ratio (SNR) in ultrasound contrast imaging.

Contrast agents for ultrasound are being developed by several pharmaceutical companies (see U.S. Pat. Nos. 5,410, 516 and 5,678,553). When injected into blood, these 1–10 um microbubbles increase the ultrasound echo strength from blood flow and perfusion (the circulation of blood to an organ or tissue). In the presence of tissue, the tissue echo strength must be significantly reduced relative to that of the contrast agent in order for flow or perfusion to be visualized. One way to suppress the tissue signal is to image the nonlinear signals generated by the microbubbles, e.g. harmonic signals, which are stronger than those generated by tissue.

Basic harmonic imaging transmits a narrowband signal at $f_0$ and then images the harmonic signal generated by contrast agents (and tissue) at $2 f_0$ by bandpass filtering (see U.S. Pat. Nos. 5,724,976 and 5,733,527). Alternatively, pulse inversion permits overlap of the fundamental and harmonic bands for better resolution by using two phase-inverted transmit pulses to cancel the fundamental (linear) component which leaves the nonlinear components to be imaged (see U.S. Pat. Nos. 5,632,277, 5,706,819, and 6,371,914).

U.S. Pat. No. 5,632,277 describes a phase inversion method using amplitude modulation. In the pulse inversion method described in U.S. Pat. No. 5,706,819, the transmitting frequency band is separated from the receiving frequency band and the harmonic component in the incident pressure wave must be suppressed to detect the harmonic response of microbubbles.

Another way to enhance the bubble signal is to excite the bubbles before imaging the bubbles. This is done by transmitting an excitation pulse separated from the imaging pulse to expand the size of the bubble to get bigger scatter cross section U.S. Pat. No. 5,833,615). U.S. Pat. No. 5,833,615 states that an excitation signal separated from the imaging signal must be transmitted before the imaging signal. As a result, either an extra transducer is needed or two separate pulses must be transmitted, reducing frame rate. Also, since the bubble signal is enhanced by exploiting the linear property of the bubble, when the method is applied to low mechanical index (MI) phase inversion imaging, the enhanced signal will be cancelled and no benefits are achieved.

Also in U.S. Pat. No. 5,833,615, an excitation enhanced ultrasound system is presented. An excitation pulse separated from the imaging pulse is used in that system to excite and thus expand the size of the microbubbles that are below 4.2 um which will increase the amount of the returned ultrasound imaging signals scattered and returned by an object (contrast bubbles). This is based on the linear property of the micro-bubbles. Thus, when applied in pulse inversion mode, the increase of the returned ultrasound imaging signals may be cancelled since it is mainly based on the increase of the scatter cross section of the bubbles which will be the same for the two phase inverted pulses.

U.S. Pat. No. 6,371,914 B1 discloses a single waveform pulse inversion method. A double-pulse excitation waveform is transmitted into the media. Normally, the two pulses in the waveform are phase-inverted. In receiving, different deconvolution functions are employed to take out the echoes from the first pulse and the second pulse, then the two echoes are realigned in time and summed to cancel a linear response. U.S. Pat. No. 6,371,914 B1 states that the waveform could be considered as a convolution of any single pulse with a known coding function.

For each of the conventional methods discussed above, the ratio of contrast to tissue signal strength is still insufficient for imaging perfusion. One method to improve the contrast-to-tissue ratio (CTR) is to reduce the transmit mechanical index since the tissue nonlinear signal falls faster than that for contrast as the mechanical index (MI) decreases. But the method quickly runs into signal-to-noise ratio (SNR) limitations.

In U.S. Pat. No. 6,213,947 B1, coded transmit pulses (chirp) are also used for single firing harmonic imaging and pulse inversion harmonic imaging modes. However, in the claims, "at least some of the received signals" need to be applied to "at least one compression filter" in single firing situation or before the combination of the received signals from the first and second transmission in the pulse inversion situation. This is significant since a compression filter is larger than a regular filter and much more expensive.

In U.S. pat. Pub. appl. No. 2002/0128555 A1, two waveform components, one selected for fundamental tissue imaging, and another one selected for tissue harmonic imaging are included in one transmit signal to simultaneously perform ultrasonic fundamental and harmonic tissue imaging. Although the inventors mentioned that this method could be used for contrast imaging, no benefit can be seen for tissue cancellation and bubble response enhancement. This method is designed for tissue harmonic imaging. For example, in the patent body, in two-transmission mode, the two transmitted bursts are only partially (one component) phase inverted; the harmonic generating component is inverted but not the fundamental component. The result is that the tissue signal is not optimally cancelled. Phase inverting both components would not provide an improvement in CTR or SNR relative to conventional wideband pulse inversion methods.

A basic need still exists to increase the CTR and SNR in ultrasound contrast imaging without extra and expensive devices. Also, low-MI imaging is desired to reduce contrast agent destruction. Contrast microbubbles are destroyed by high-MI ultrasound pulses, therefore, low-MI pulses are desired in order to not destroy contrast agents and in order to maintain a longer duration over which the contrast agents may be imaged.

SUMMARY OF THE INVENTION

An embodiment of the present invention provides a method and apparatus in an ultrasound imaging system for performing contrast imaging by enhancing the CTR and SNR using stepped-chirp waveforms.

A method is provided in an ultrasound imaging system which comprises generating a single stepped-chirp transmit pulse that includes a first waveform component centered at a first frequency, and at least a second waveform component centered at least at a second frequency. The first waveform component is employed with a first frequency optimized to initiate the bubble dynamics and the second waveform component is employed with a second frequency optimized to produce an enhanced bubble nonlinear response. Typically, the second frequency is greater than the first frequency. The first waveform component may be placed before the at least a second waveform component within the single stepped-chirp transmit pulse. Alternatively, the at least a second waveform component may be added to the first waveform component within the single stepped-chirp transmit pulse. At least one of a center frequency, an amplitude, a starting phase, and a bandwidth of the first waveform component and the at least a second waveform component are adjusted to generate the single stepped-chirp transmit pulse. A relative phase, a switch time, and a time delay between the first waveform component and the at least a second waveform component are also adjusted. Received signals are generated from echoes of the single stepped-chirp transmit pulse reflected from at least one of contrast agent bubbles, tissue, and blood. The received signals are processed to generate display signals that are displayed as an image.

An apparatus is provided in an ultrasound imaging system which comprises a transmitter subsection to generate and transmit a stepped-chirp waveform, and a receiver subsection to generate received signals by receiving, beamforming, and filtering echoes of the stepped-chirp waveform reflected from at least one of contrast bubbles, tissue, and blood. Also, a processing subsection is provided to integrate, scan convert, and display the received signals as an image. The transmitter subsection comprises a transmitter, a stepped-chirp waveform generator, and a transmitter controller. The receiver subsection comprises a receiver, a beamformer, a receiver controller, and a memory. The processing subsection comprises a signal processor, a scan converter, and a display.

Certain embodiments of the present invention afford an approach to enhance the CTR and SNR in a contrast image using stepped-chirp waveforms.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION

An embodiment of the present invention enables enhanced contrast imaging in an ultrasound system using stepped-chirp waveforms to enhance CTR and SNR. Stepped-chirp is a form of frequency modulation.

A shell-encapsulated micro-sized bubble vibrating spherically when driven by an incident pressure wave inside an infinite liquid can be modeled as a linear mass-spring system when the driving pressure is very low (e.g. <30 kpa). As a result, the pressure on the surface of the bubble, $P_L$, generated by the effective "stiffness" of the bubble spring-mass system may be proportional to the bubble wall displacement $\epsilon_a = a - a_e$, where $a_e$ is the equilibrium radius of the bubble, and a is the instantaneous bubble radius. However, when the driving pressure is high (e.g. >30 kpa), the bubble begins to respond nonlinearly and the linear mass-spring system may no longer describe the bubble motion. Then the surface pressure $P_L$ is no longer proportional to bubble radial displacement $\epsilon_a$. The nonlinear relation between the bubble surface pressure $P_L$ and the radial displacement $\epsilon_a$ is calculated for a 4 um shell-encapsulated bubble and plotted in FIG. 1.

Figure 1:
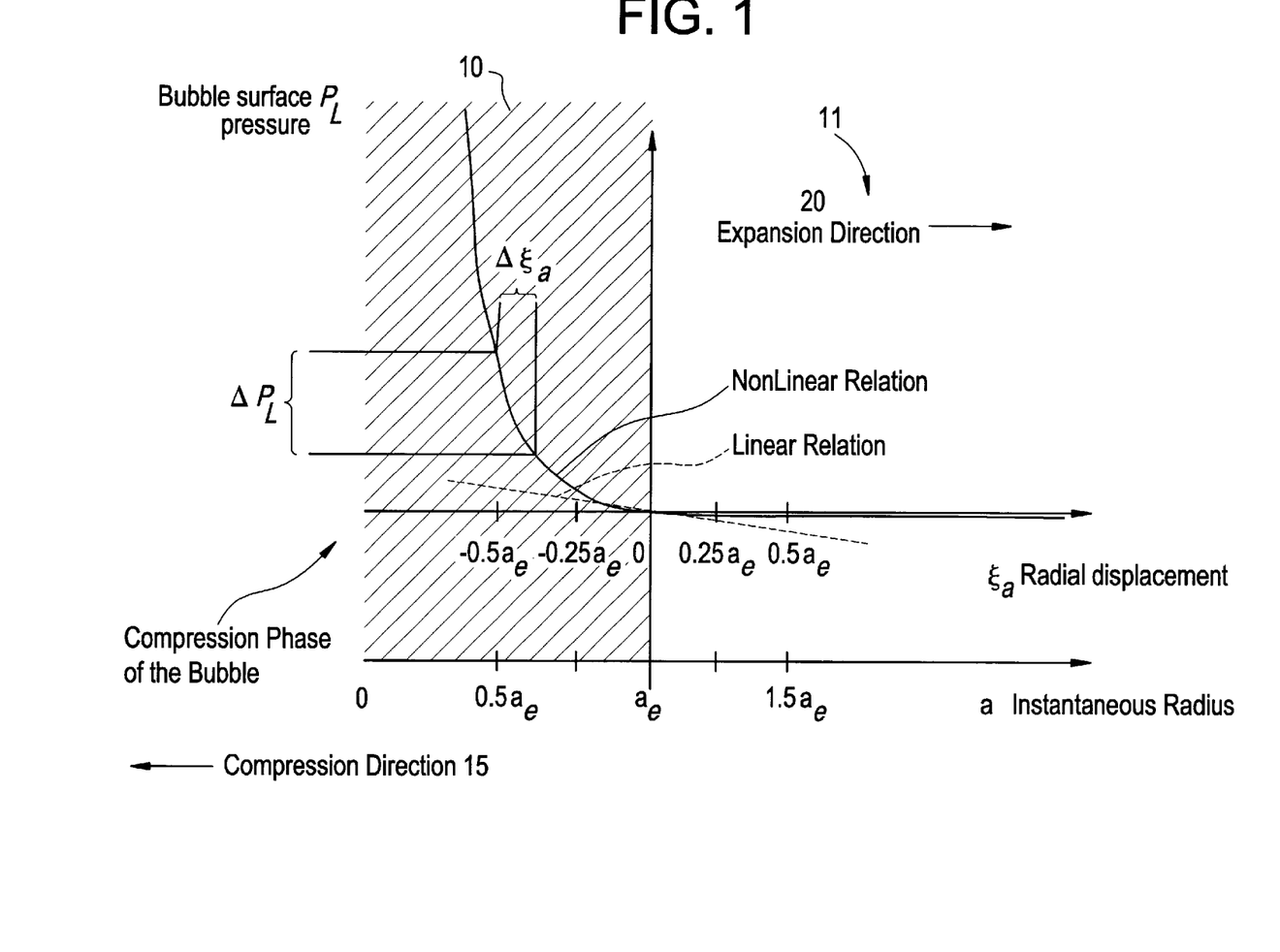
FIG. 1 is an illustration of bubble surface pressure as a function of radial displacement in nonlinear vibration as exploited in accordance with an embodiment of the present invention.

From FIG. 1, it can be seen that in the compression phase 10, when bubble size $a < 0.75\ a_e$ (bubble displacement $\epsilon_a < -0.25 a_e$), a small radial displacement $\Delta\epsilon_a$ in the compression direction 15 will cause a huge surface pressure change $\Delta P_L$. On the contrary, when the bubble size $a > 1.25\ a_e$ (bubble displacement $\epsilon_a > 0.25\ a_e$), a small or even a big radial displacement in the expansion direction 20 will cause almost no change in the surface pressure compared to the bubble radius compression phase.

Now consider the wave scattered from the bubble vibration in the far field:

$$p_s(r,t)|_{far\text{-}field} = \frac{a}{r}\left(\frac{1}{2}p\dot{a}^2 + p_L(t) - p_0 - p_i(t)\right), \quad (1)$$

where r is the distance between observer point and the bubble center, ȧ is the bubble wall velocity, $p_i$ (t) is the incident pressure, $P_0$ is the hydrostatic pressure in the liquid, and p is the liquid density. It is clear that the higher $P_L$ generated in the bubble vibration, the higher amplitude the scattered wave will be. Also, higher bubble wall velocity also helps enhance the scattered wave. Since the scattered wave is very nonlinear, a higher amplitude scattered wave results in an enhancement of fundamental and higher order harmonic components. Thus, from the analysis based on FIG. 1, much stronger bubble nonlinear response may be acquired by stronger compression.

Given the nonlinear property of the bubble, there are several ways to enhance the bubble nonlinear response. One way is to simply increase the amplitude of the incident pressure. However, many clinical applications with contrast agents need to work at a low MI state to prevent bubble destruction. As a result, the highest pressure amplitude that may be applied is limited. The other way is to try to compress the bubble over a longer time, which means transmitting a lower frequency waveform in the normal sense. However, lower frequency yields low lateral resolution and thus poor image quality and, therefore, is not a practical solution.

An embodiment of the present invention uses the bubble nonlinear property by designing a special waveform—a stepped-chirp waveform. The stepped-chirp waveform is a combination of a first waveform component 50 (centered at frequency $f_l$) and a second waveform component 60 (centered at frequency $f_h$) in one pulse. The first waveform component is employed with an optimized frequency to initiate the bubble dynamics and the second waveform component is employed with an optimized second frequency to produce an enhanced bubble nonlinear response. By adjusting the center frequency, amplitude, and bandwidth for the two wave components of the stepped-chirp waveform and their relative phase, frequency, switch time (the time point where the waveform changes from one frequency to another) and the time delays in between, the nonlinear response of the bubble may be enhanced.

Figure 2:
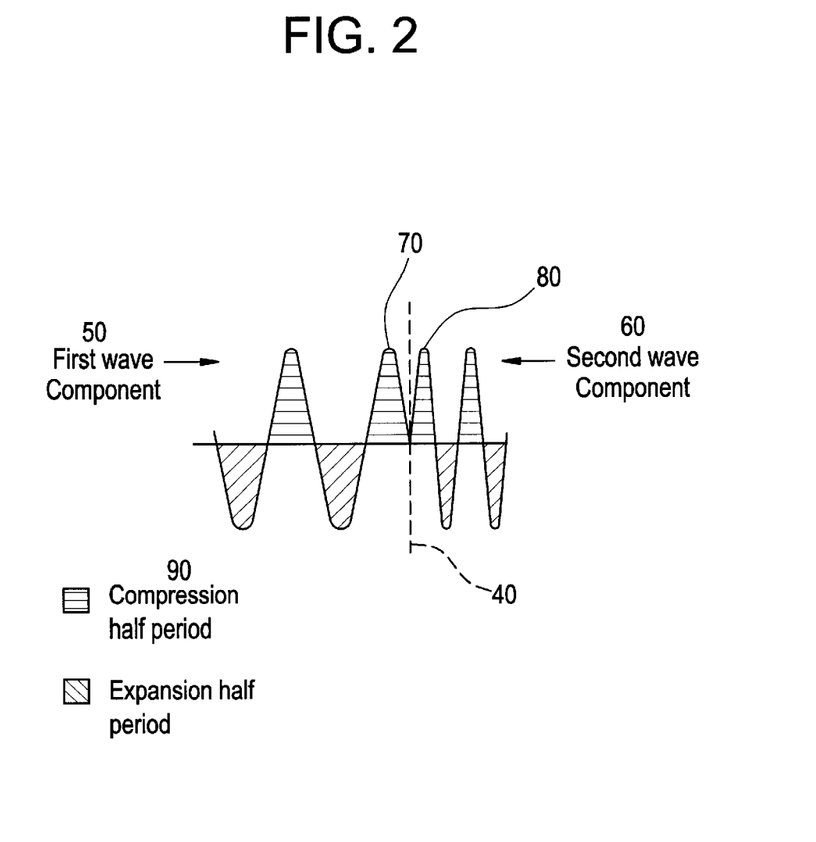
FIG. 2 is an exemplary illustration of a stepped-chirp pulse in accordance with an embodiment of the present invention.
Figure 3A:
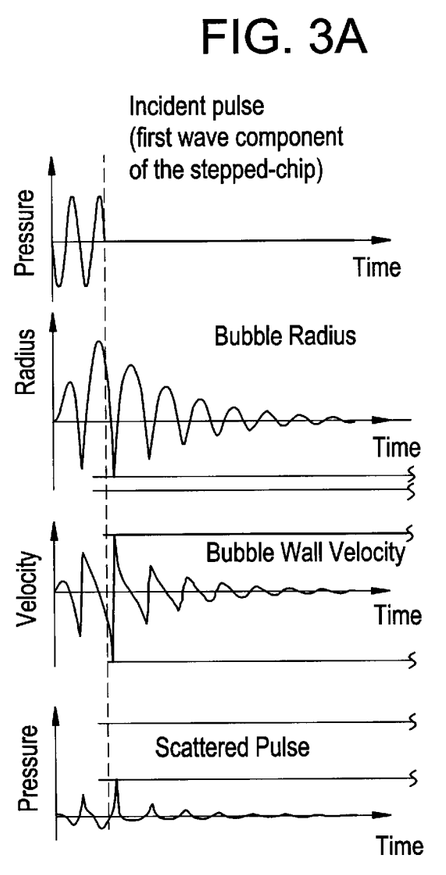
FIG. 3 is an exemplary illustration of simulated bubble responses in accordance with an embodiment of the present invention.
Figure 3B:
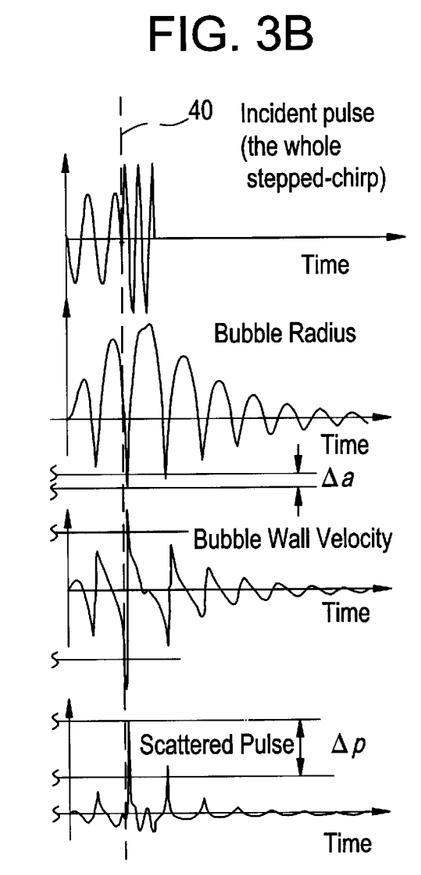

Specifically, the two wave components may be combined in such a way that both the end half period 70 of the first wave component 50 and the beginning half period 80 of the second wave component 60 are in the compression half period 90 as shown in FIG. 2. The combination of waveform components imparts a longer compression time to the bubble without using a much lower frequency. As a result, more bubble radial displacement and higher bubble wall velocity in the compression phase may be achieved resulting in a much stronger scattered wave generated just after the switch time 40. FIG. 3 shows the simulated bubble responses with: a). transmitting just the first wave component of the stepped-chirp waveform; b). transmitting the entire stepped-chirp waveform.

Notice a small difference in bubble radius Δa in the compression phase corresponding to a big change Δp in the scattered wave amplitude. Also notice the increase of the bubble wall velocity after introducing the second wave component. In (a), the dashed line locates where the pulse stops. In (b), the dashed line 40 locates where the waveform switched from the low frequency component to the high frequency component.

In the design of the stepped-chirp waveform, although a longer compressing time is expected to enhance the bubble nonlinear response, the first half compression period of the second wave component 60 needs to be short enough to avoid negative interaction with the bubble expansion phase. Under such a limitation, the first half compression period 80 of the second wave component 60 may be shorter than the end half compression period 70 of the first wave component 50 since there is no requirement to change the direction of the bubble wall velocity (see FIG. 3) and the bubble surface pressure increases very fast in the compression phase. As a result, the relation $f_h > f_l$ is chosen. Therefore, an embodiment of the present invention comprises an upward stepped-chirp waveform. From now on, the first wave component 50 is referred to as the low frequency wave component and the second wave component 60 as the high frequency wave component.

Low-MI imaging is desired to reduce contrast agent destruction. Contrast microbubbles are destroyed by high-MI ultrasound pulses, therefore, low-MI pulses are desired in order to not destroy contrast agents and in order to maintain a longer duration over which the contrast agents may be imaged. Stepped-chirp waveforms may be designed to provide low-MI imaging.

Figure 4:
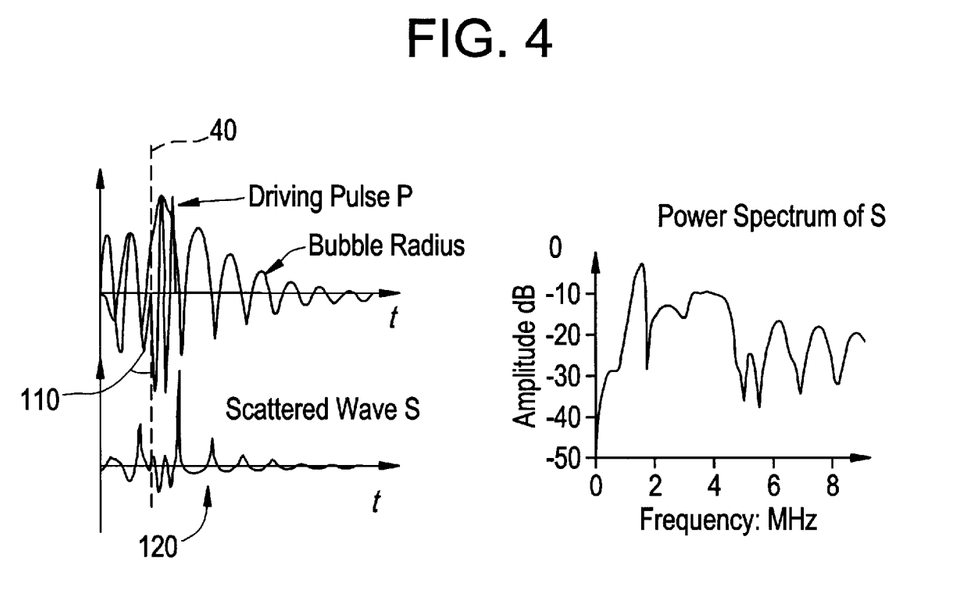
FIG. 4 is an exemplary illustration of results of using a stepped-chirp pulse in single firing harmonic imaging in accordance with an embodiment of the present invention.

The stepped-chirp waveform may be designed specially for single firing harmonic contrast imaging. In such a case, $f_h$ may be around $2f_l$ and echoes may be filtered around $2f_l$ upon reception. To obtain a stronger response around the second harmonic frequency, instead of two continuous compression half periods as shown in FIG. 2, two continuous expansion periods 110 may be employed at the switch time 40 as shown in FIG. 4.

During the expansion phase 11, the bubble acts more like a linear mass-spring system since the radial displacement does not cause large surface pressure changes (see FIG. 1 and Equation 1). Therefore, more energy around the driving frequency (i.e., $2f_l$) is scattered. Also, since the scatter cross-section is proportional to the square of the bubble size, a higher amplitude scattered wave may be expected than using the $2f_l$ frequency wave to drive a static bubble. The nonlinear response of the bubble is also strengthened since the second compression period of the high frequency wave component is in phase with bubble compression and results in more compression displacement and higher bubble wall velocity. Therefore, a stronger scattered wave 120 is achieved shortly after that half period as shown in FIG. 4. The total bubble response around $2f_l$ will be the combination of the enhanced nonlinear response and linear response around $2f_l$. A higher CTR may be achieved because of the enhanced nonlinear response and also, since even at linear phase, bubbles still give stronger scattering than tissue because the bubbles have much larger compressibility than tissue. A higher SNR may also be achieved since the amplitude of the scattered wave 120 is much stronger than just transmitting a low frequency wave centered at $f_l$ which has the same length as the stepped-chirp waveform.

Figure 5:
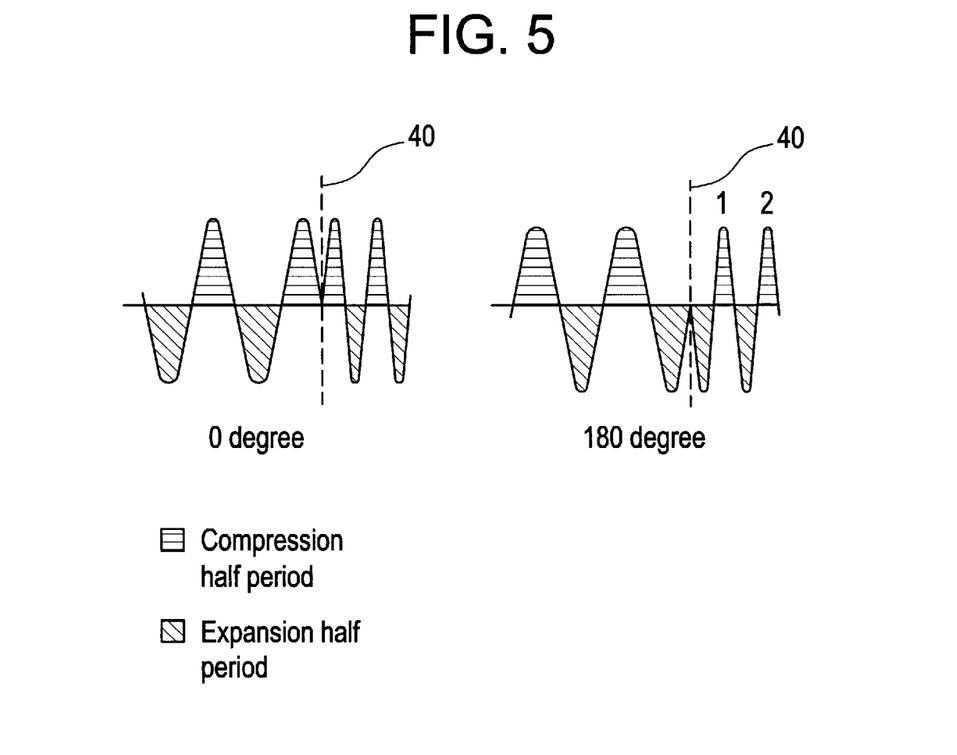
FIG. 5 is an exemplary pair of phase inverted stepped-chirp pulses in accordance with an embodiment of the present invention.

A natural application of the nonlinear relation between bubble surface pressure and the bubble radius displacement is to enhance pulse inversion imaging using a pair of phase-inverted stepped-chirp waveforms. In an embodiment of the present invention, if the stepped-chirp waveform in FIG. 2 is defined as the 0 degree pulse and the phase-inverted version of the 0 degree pulse is defined as the 180 degree pulse as shown in FIG. 5, then it is clear that the 180 degree pulse gives a longer time of expansion around the switch time 40 as shown in FIG. 5.

However, as shown in FIG. 1, during the bubble expansion phase 11, a radius displacement in the expansion direction 20 causes almost no change in bubble surface pressure compared to the same amount of displacement in the bubble compression phase 10. As a result, the scattered wave from the bubble in 180 degree pulse transmission is not enhanced as much as in 0 degree pulse transmission. For tissue, because of the much weaker nonlinearity compared to bubbles, no significant difference may be found between the echoes from the 0 degree transmission and the 180 degree transmission. Thus, CTR and SNR may be enhanced in receiving after coherent summation of the echo signals from the ultrasonic contrast agent and the tissue in the two phase-inverted stepped-chirp transmissions.

Figure 6:
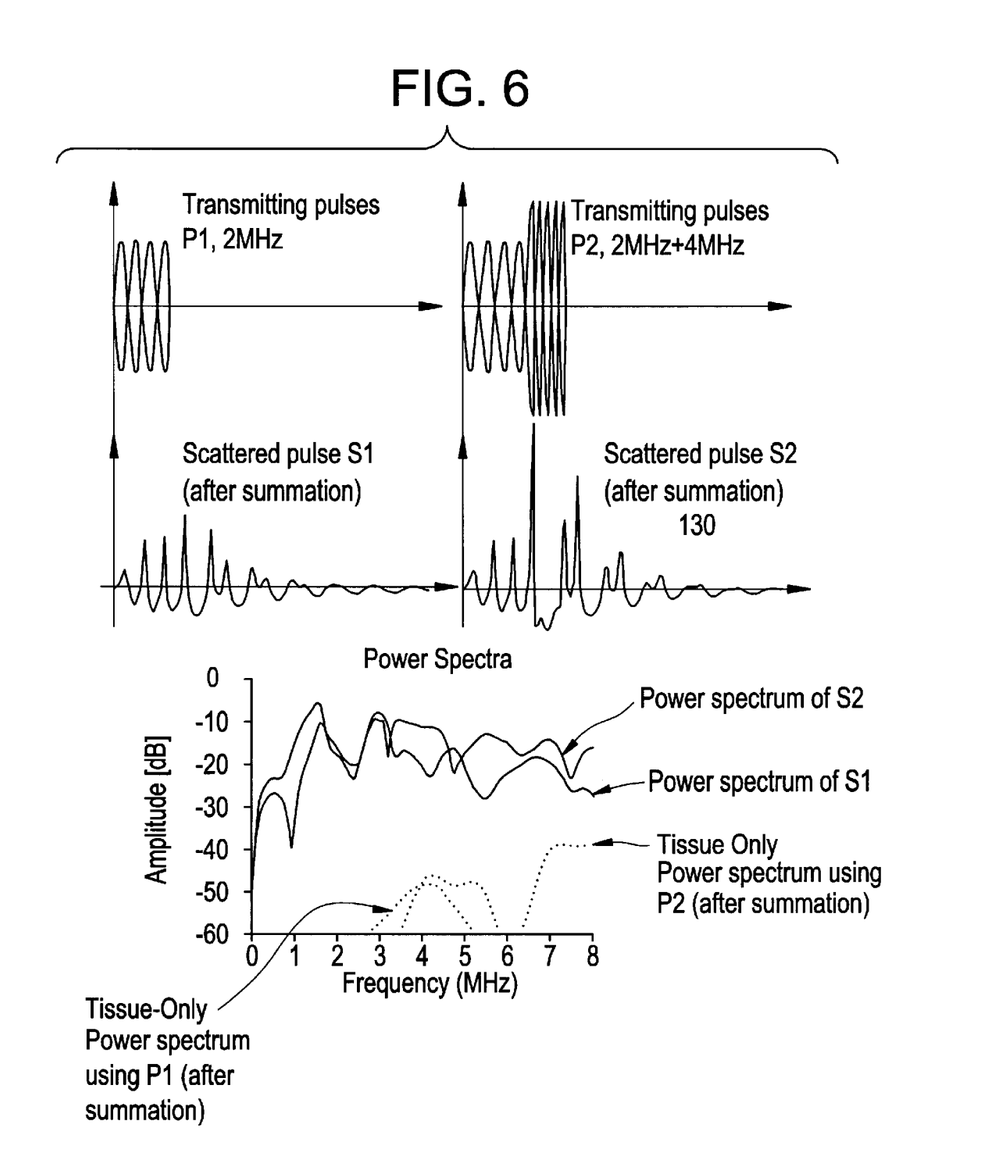
FIG. 6 is an exemplary illustration of simulated enhancement of pulse inversion imaging using a pair of phase-inverted stepped-chirp pulses in accordance with an embodiment of the present invention.

Specifically, when $f_h$ is around $2f_l$, strong enhancement may be achieved around $2f_l$ compared to just using a pair of phase-inverted low frequency components of the stepped-chirp as in regular phase-inversion imaging. The received echoes from the first and the second firings may be filtered around $2f_l$ before or after coherent summation to get strong CTR. FIG. 6 shows simulated results of the scattered wave 130 (after coherent summation) and power spectrum with 2 MHz regular phase-inversion imaging and with 2 MHz and 4 Mhz stepped-chirp-imaging. About 7 to 8 dB enhancement is achieved around 4 MHz using a pair of phase-inverted stepped-chirp waveforms.

Figure 7:
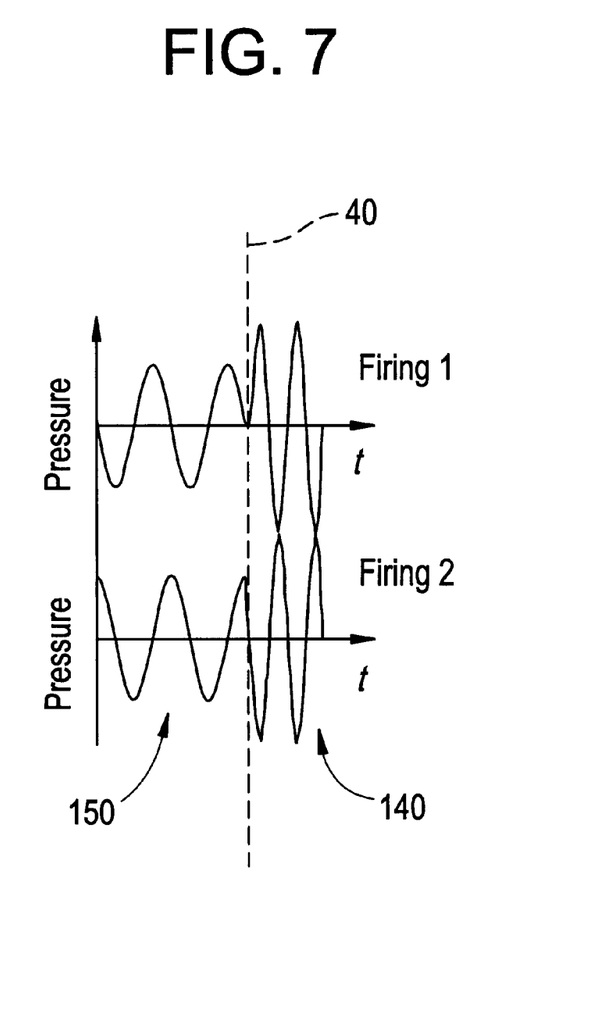
FIG. 7 is an exemplary illustration of a pair of stepped-chirp pulses that are not totally phase-inverted in accordance with an embodiment of the present invention.

In an embodiment of the present invention, the stepped-chirp waveform may also be used in multiple-firing (including single firing and double firings) situations with phase or amplitude coded transmission waves. For double firings, the two pulses may not need to be totally phase inverted, e.g. there may be one part 140 of the second waveform inverted, while another part 150 is not inverted, as shown in FIG. 7 (a pair of stepped-chirp waveforms that are not totally phase-inverted . . . first part 90 degree phase shifted, second part inverted). Also, notice that the amplitudes of the two components are different. Each stepped-chirp waveform may be a combination of two or more discrete frequency components. The combination may be one component simply following the other component or one component adding to another component on top of itself or on part of itself.

Figure 8:
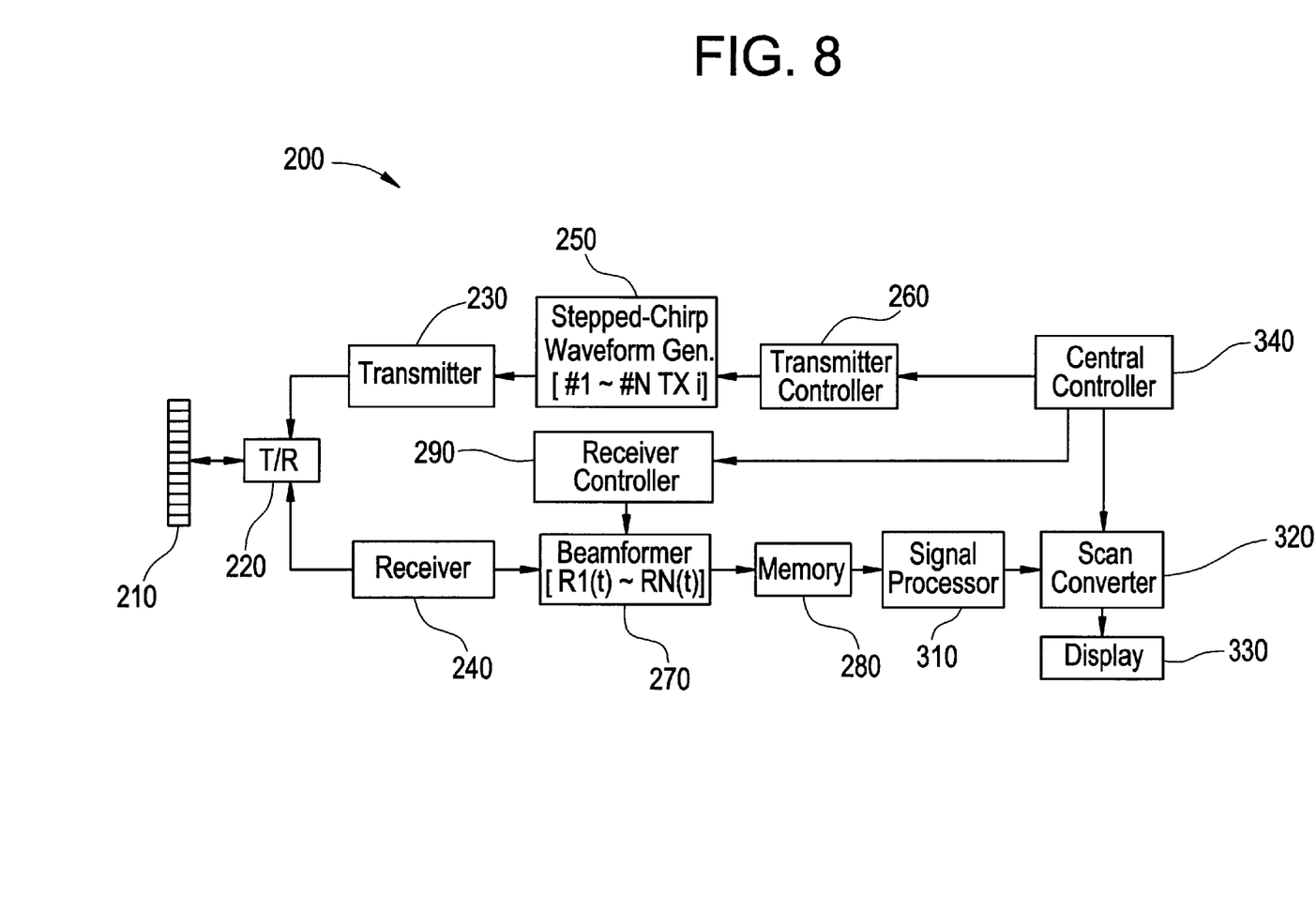
FIG. 8 illustrates a schematic block diagram of an ultrasound imaging system for performing enhanced contrast imaging using stepped-chirp pulses in accordance with an embodiment of the present invention.

FIG. 8 illustrates a block diagram of an ultrasonic diagnostic imaging system 200 constructed in accordance with an embodiment of the present invention. The system includes a transducer array 210 that is coupled via a transmit/receive switch 220 with a transmitter 230 and receiver 240. Stepped-chirp waveforms [#1~#N] (N=1, 2, . . . ) are transmitted sequentially via stepped-chirp waveform generator 250 and transmitter 230 controlled by transmitter controller 260.

Figure 9:
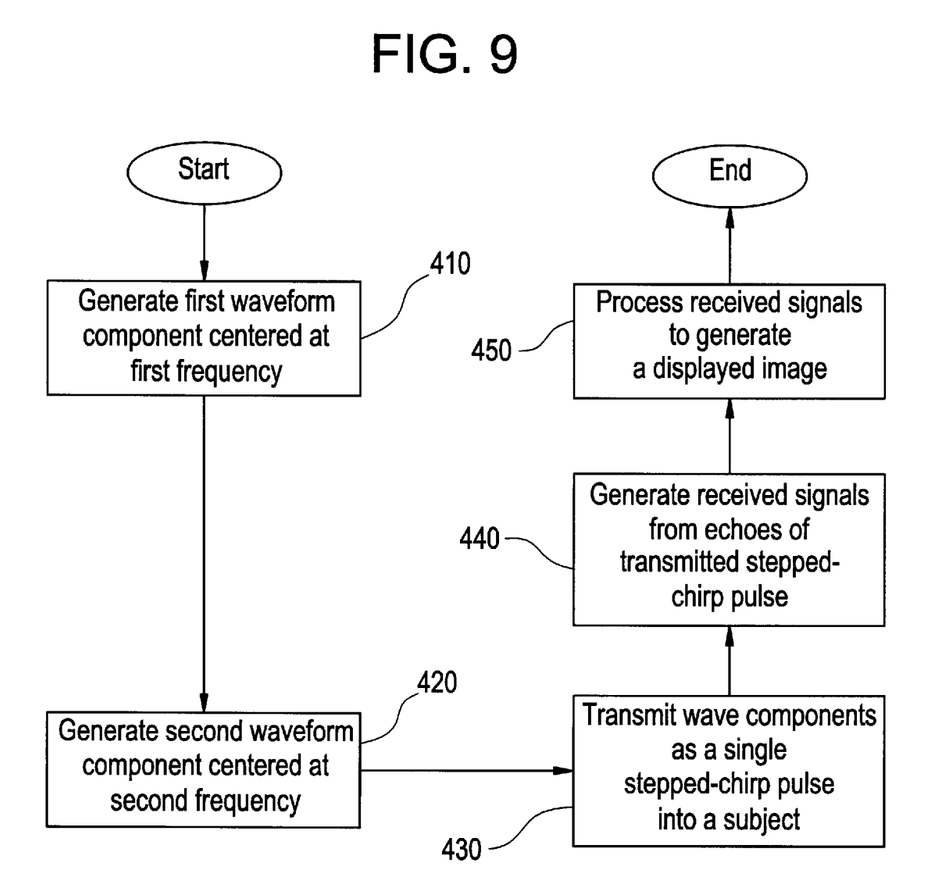
FIG. 9 illustrates a flow chart of a method for performing enhanced contrast imaging using stepped-chirp pulses in accordance with an embodiment of the present invention.

For a single pulse K, referring to FIG. 8 and FIG. 9, in steps 410 and 420, the stepped-chirp waveform generator 250 generates a single stepped-chirp pulse with a first waveform component centered at a first center frequency and at least a second waveform component centered at least at a second frequency.

Specifically, there are at least two ways to generate the single stepped-chirp pulse: 1. design the stepped-chirp pulse offline then generate the whole single stepped-chirp pulse K and save it in the transmit memory for transmitting. 2. generate the first waveform component at a first frequency, then generate at least a second waveform component at least at a second frequency separately, and then combine the at least two waveform components as a single stepped-chirp pulse K.

In step 430, the generated single stepped-chirp pulse K is transmitted into a subject by transmitter 230 through transducer array 210. In step 440, receiver 240 and beamformer 270 generate received signals from the echoes of the reflected stepped-chirp pulse and store the received signals in memory 280. A compression filter is not used upon reception. In step 450, the received signals are processed to generate a displayed contrast image.

In an embodiment of the present invention, the bandwidth and center frequency of the receive bandpass filter of the receiver 240 may be adjusted to obtain the best contrast response. For example, the center frequency may be one of the transmit frequencies (each waveform component has its own transmit frequency), or one of the subharmonic, ultraharmonic, second harmonic or higher order harmonics of one of the transmit frequencies. The receive bandwidth may be broad enough to include one or more than one of the frequency bands described above.

"Multiple stepped-chirp pulses may be generated. A stepped-chirp pulse K+1 (K∈{1, N−1}) is transmitted after echoes from transmitted stepped-chirp pulse K is received. The echoes from each firing are received sequentially by receiver 240. The received signals {R1–RN} are each beamformed and filtered by beamformer 270 and stored in memory 280, controlled by receiver controller 290. In step 450, after the N number of received signals are acquired, they are integrated together by signal processor 310 (including coherent summation). Then the resultant processed signals are sent to the scan converter 320 and finally displayed on the monitor of display 330. The central controller 340 coordinates all higher-level functions of the ultrasound imaging system."

As an alternative embodiment of the present invention, received echoes reflected from all or some of the transmitted stepped-chirp pulses may be coherently summed before beamforming and filtering.

As a further alternative embodiment of the present invention, a stepped-chirp pulse having more than two waveform components may be generated and transmitted. For example, a stepped-chirp pulse may have three waveform components each at a different center frequency.

In summary, CTR and SNR may be enhanced during ultrasound contrast imaging using stepped-chirp waveforms. The stepped-chirp waveforms are designed to exploit the nonlinear properties of the contrast bubbles and not for fundamental or harmonic tissue imaging. The stepped-chirp waveforms are composed of at least two components centered at different frequencies and cannot be derived by convolving any single pulse with a known coding function. A compression filter is not used in the reception process. Also, the receiving frequency band may mostly overlap the transmitting frequency band (i.e. there may not be a distinct separation of the receiver frequency band and the transmitting frequency band).

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. In an ultrasound imaging system, a method to increase a contrast-to-tissue ratio and a signal-to-noise ratio for ultrasound contrast imaging of a subject, said method comprising:

generating a single stepped-chirp transmit pulse that includes a first waveform component centered at a first frequency optimized to initiate contrast bubble dynamics, and at least a second waveform component centered at least at a second frequency optimized to produce an enhanced contrast bubble nonlinear response; and transmitting said single stepped-chirp transmit pulse into said subject.

2. The method of claim 1 wherein said second frequency is greater than said first frequency.

3. The method of claim 1 wherein said second frequency is smaller than said first frequency.

4. The method of claim 1 wherein said second frequency is about twice said first frequency.

5. The method of claim 1 wherein an amplitude of said first waveform component is different from an amplitude of said at least a second waveform component.

6. The method of claim 1 further comprising placing said first waveform component before said at least a second waveform component within said single stepped-chirp transmit pulse.

7. The method of claim 1 further comprising adding said at least a second waveform component to said first waveform component within said single stepped-chirp transmit pulse.

8. The method of claim 1 wherein an end half period of said first waveform component and a beginning half period of said at least a second waveform component are in a compression half period of said single stepped-chirp transmit pulse.

9. The method of claim 1 wherein an end half period of said first waveform component and a beginning half period of said at least a second waveform component are in an expansion half period of said single stepped-chirp transmit pulse.

10. The method of claim 1 wherein said generating comprises adjusting at least one of a center frequency, an amplitude, a starting phase, and a bandwidth of said first waveform component and said at least a second waveform component.

11. The method of claim 1 wherein said generating comprises adjusting a relative phase, a switch time, and a time delay between said first waveform component and said at least a second waveform component.

12. The method of claim 1 wherein a first half compression period of said at least a second waveform component is shorter in time duration than an end half compression period of said first waveform component.

13. The method of claim 1 further comprising:

generating received signals from echoes of said single stepped-chirp transmit pulse reflected from at least one of contrast agent bubbles, tissue, and blood;

processing said received signals to generate display signals; and generating a displayed image from said display signals.

14. The method of claim 1 further comprising:

generating received signals from echoes of said single stepped-chirp transmit pulse reflected from at least one of contrast agent bubbles, tissue, and blood; and filtering said received signals around said second frequency of said second waveform component.

15. The method of claim 1 wherein a receiving frequency band mostly overlaps a transmitting frequency band of said single stepped-chirp transmit pulse.

16. The method of claim 1 further comprising receiving and filtering signals from echoes of said single stepped-chirp transmit pulse at a center frequency comprising one of:

a center frequency of a waveform component of said transmit pulse;

a subharmonic frequency of a waveform component of said transmit pulse;

an ultraharmonic frequency of a waveform component of said transmit pulse;

a second harmonic frequency of a waveform component of said transmit pulse; and a higher order harmonic frequency of a waveform component of said transmit pulse.

17. The method of claim 1 further comprising receiving and filtering signals from echoes of said single stepped-chirp transmit pulse within a bandwidth comprising at least one of:

a center frequency of a waveform component of said transmit pulse;

a subharmonic frequency of a waveform component of said transmit pulse;

an ultraharmonic frequency of a waveform component of said transmit pulse;

a second harmonic frequency of a waveform component of said transmit pulse; and a higher order harmonic frequency of a waveform component of said transmit pulse.

18. The method of claim 1 further comprising transmitting at least one stepped-chirp transmit pulse after said single stepped-chirp transmit pulse.

19. The method of claim 1 further comprising:

transmitting at least one stepped-chirp transmit pulse after said single stepped chirp transmit pulse;

generating received signals from echoes of said single stepped-chirp transmit pulse and said at least one stepped-chirp transmit pulse; and processing said received signals to generate a displayed image.

20. The method of claim 1 further comprising transmitting a phase-inverted transmit pulse after said single stepped-chirp transmit pulse wherein said phase-inverted transmit pulse is a 180 degree phase inversion of said single stepped-chirp transmit pulse.

21. The method of claim 1 further comprising transmitting a partially phase-inverted stepped-chirp transmit pulse after said single stepped-chirp transmit pulse wherein only one waveform component of said partially phase-inverted stepped-chirp transmit pulse is phase inverted 180 degrees from a corresponding waveform component of said single stepped-chirp transmit pulse.

22. The method of claim 1 further comprising injecting an ultrasound contrast agent into said subject.

23. In an ultrasound imaging system, apparatus to increase a contrast-to-tissue ratio and a signal-to-noise ratio for ultrasound contrast imaging, said apparatus comprising:
   a transmitter subsection to generate and transmit at least one stepped-chirp waveform into a subject wherein said at least one stepped-chirp waveform includes a first waveform component centered at a first frequency optimized to initiate contrast bubble dynamics, and at least a second waveform component centered at least at a second frequency optimized to produce an enhanced contrast bubble nonlinear response;
   a receiver subsection to generate received signals by receiving, beamforming, and filtering echoes of said at least one stepped-chirp waveform reflected from at least one of contrast bubbles, tissue, and blood; and
   a processing subsection to integrate, scan convert, and display said received signals as an image.

24. The apparatus of claim 23 wherein said receiver subsection coherently sums echoes of said at least one stepped-chirp waveform before said beamforming and said filtering and wherein said at least one stepped-chirp waveform comprises more than one stepped-chirp waveform.

25. The apparatus of claim 23 wherein said receiver subsection coherently sums echoes of said at least one stepped-chirp waveform after said beamforming and said filtering and wherein said at least one stepped-chirp waveform comprises more than one stepped-chirp waveform.

26. The apparatus of claim 23 wherein said transmitter subsection comprises a transmitter, a stepped-chirp waveform generator, and a transmitter controller.

27. The apparatus of claim 23 wherein said receiver subsection comprises a receiver, a beamformer, a receiver controller, and a memory.

28. The apparatus of claim 23 wherein said receiver subsection comprises a bandpass filter whose bandwidth may be adjusted to improve a contrast response.

29. The apparatus of claim 23 wherein said processing subsection comprises a signal processor, a scan converter, and a display.

30. The apparatus of claim 23 further comprising a central controller to coordinate higher-level functions of said ultrasound imaging system.

31. The apparatus of claim 23 further comprising a transmit/receive switch to route transmit signals to a transducer array during a transmit phase and to route echo signals to said receiver subsection during a receive phase.

32. The apparatus of claim 23 further comprising a transducer array to convert electrical energy to ultrasound energy and ultrasound energy to electrical energy.

* * * * *

UNITED STATES PATENT AND TRADEMARK OFFICE
CERTIFICATE OF CORRECTION

PATENT NO. : 6,953,434 B2
DATED : October 11, 2005
INVENTOR(S) : Hao et al.

It is certified that error appears in the above-identified patent and that said Letters Patent is hereby corrected as shown below:

Column 8,
Line 37, before "Multiple" delete """".
Line 52, after "system" delete """".

Signed and Sealed this

Twenty-fifth Day of April, 2006

JON W. DUDAS
*Director of the United States Patent and Trademark Office*